United States Patent [19]

Workman

[11] Patent Number: 5,017,615

[45] Date of Patent: May 21, 1991

[54] FLEA KILLER COMPOSITIONS

[76] Inventor: Lester J. Workman, P.O. Box 5547, Sarasota, Fla. 34277-5547

[21] Appl. No.: 143,954

[22] Filed: Jan. 14, 1988

[51] Int. Cl.$^5$ .................. A01N 35/00; A01N 37/00; A01N 37/36; A01N 57/10

[52] U.S. Cl. .................. 514/560; 514/144; 514/159; 514/557; 514/693; 514/716; 514/724; 514/731

[58] Field of Search ............................ 514/560

[56] References Cited

U.S. PATENT DOCUMENTS

| | | | |
|---|---|---|---|
| 3,445,565 | 5/1969 | Locher et al. | 514/560 |
| 4,447,423 | 5/1984 | Workman | 514/163 |
| 4,731,379 | 3/1988 | Panzer | 514/547 |

OTHER PUBLICATIONS

King; Chemicals Evaluated as Insecticides and Repellants at Orlando, Fla., May 1954, pp. 1-17, 184 and 185.

*Primary Examiner*—Allen J. Robinson
*Attorney, Agent, or Firm*—Cushman, Darby & Cushman

[57] ABSTRACT

The present invention relates to improved insecticidal compositions which are effective in eliminating or controlling ectoparasites, such as fleas, on domestic animals without detrimental side effects to the host. The compositions each comprise a low grade flea killer in conjuction with a surfactant and may optionally include a solvent or group of solvents to improve the miscibility of the composition.

3 Claims, No Drawings

FLEA KILLER COMPOSITIONS

BACKGROUND OF THE INVENTION

The present invention relates to improved insecticidal compositions for the control of ectoparasites, such as fleas, on domestic animals, i.e., dogs and cats.

Various washes and shampoos have been proposed in the art for controlling ectoparasites, such as fleas, on domestic animals. However, the prior art has not disclosed an insecticidal composition which is effective in controlling fleas on domestic animals without entailing significant disadvantages. These disadvantages include detrimental side effects to the host, including allergic sensitivity reactions as evidenced by the animal's skin and/or fur and difficulty in use (for example, lengthy soak times to enhance the effectiveness of the insecticidal composition).

A series of experiments conducted by the United States government has determined that a number of chemicals, i.e., BHC (benzene hexachloride), chlordane, dinitro ortho-cresol, DDT (dichlorodiphenyltrichloroethene), dioctylamine, heptachlor, parathion, dinitro butyl phenol, paraoxon and lethane, effectively control fleas on domestic animals. However, all of these chemicals have been found to be extremely harmful to the host.

Further tests have determined that a number of low grade flea killers, i.e., para-nitroanisole, capric acid, hendecenoic acid, nonyl alcohol, nonyl phenol, tributyl phosphate, butyl salicylate, amyl salicylate, bromo methyl salicylate, hexyl salicylate and valeraldehyde, among others, effect fleas and are not harmful to the host. However, these chemicals have not been found to be sufficiently effective in the control of fleas.

Among the objects of the present invention is the provision of an insecticidal composition which is suitable for application directly to an animal's body and which will eliminate or effectively control fleas without detrimental side effects to the host.

The foregoing as well further objects of the present invention will be more fully understood from the following description.

DESCRIPTION OF THE INVENTION

After numerous experiments, I have discovered that when one or more low grade flea killers are used in conjunction with a surfactant or mixture of surfactants, and optionally a solvent or solvent mixture to improve the miscibility of the composition, the resultant non-toxic insecticidal composition eliminates or effectively controls fleas, to a greater extent than the toxic flea killers described above. The insecticidal compositions of the present invention are not harmful to either animals or humans. Apparently the surfactant causes the insects' nerve sheath to become more permeable and allows the other ingredients in the composition to alter or destroy the nerve cells.

The insecticidal compositions of my invention comprise one or more of any low grade flea killer. Examples of low grade flea killers which may be used according to the present invention include, but are not limited to, para-nitroanisole, capric acid, hendecenoic acid, nonyl alcohol, nonyl phenol, tributyl phosphate, butyl salicylate, amyl salicylate, bromo methyl salicylate, hexyl salicylate and valeraldehyde.

Suitable surfactants include any of the synthetic detergents which are readily available in commerce and which are described in the literature; for example, in "Surface Active Agents and Detergents," Volumes 1 and 2 by Schwartz, Perry and Berch. Generally stated, the surface active component of an insecticidal composition of my invention may include a synthetic ionic, nonionic, amphoteric or zwitterionic compound, or a mixture of two or more of these compounds. Preferably, cationic, anionic and/or nonionic compounds are used.

A solvent or group of solvents may optionally be included in an insecticidal composition of my invention in order to improve its miscibility. Suitable solvents include water, an alcohol, an ester, glycerol and/or a ketone e.g. acetone, among others.

The method of my invention comprises applying to an infested animal an insecticidally effective amount of a composition of the present invention. The insecticidal composition, which is typically a shampoo or like liquid, is applied to the animal's body while the fur is still dry. The shampoo or equivalent composition is rubbed into the fur until lathering begins. The composition thus applied is allowed to remain in contact with the animal's skin and fur for a period of time to at least control and preferably eradicate the ectoparasites contained thereon. The insecticidal composition is then rinsed off the animal's skin and fur.

Instead of being used as a shampoo, the composition may be suitably diluted and used as a spray on the animal or on furniture, carpets or the like to kill fleas or flea larva.

It will be understood that while my invention has been described with respect to eradicating and controlling insect infestations in domestic animals (in particular, fleas on dogs and cats) there are numerous other applications to which the compositions of my invention may be put.

The present invention is illustrated in detail in the following example. This example is included for illustrative purposes and should not be considered to limit the present invention.

EXAMPLE

An insecticidal composition was prepared as follows:

| Compound | Percent Composition, % |
| --- | --- |
| Dioctyl Sodium Sulfosuccinate | 12 |
| Hendecenoic Acid | 2 |
| Ethyl Alcohol | 20 |
| Water | 66 |

A similar composition may include acetone or other ketone as a replacement for some or all of the ethyl alcohol.

What is claimed is:

1. An insecticidal composition for eliminating or controlling ectoparasites on domestic animals, said insecticidal composition consisting essentially of about 12% disctyl sodium sulfosuccinate, about 2% hendecensic acid and a solvent or group of solvents.

2. The insecticidal composition of claim 1, wherein the solvent is water, an alcohol, an ester, glycerol or a ketone.

3. An insecticidal composition according to claim 1, wherein the solvents are ethyl alcohol and water.

* * * * *